United States Patent
Abraham et al.

(10) Patent No.: US 10,049,457 B2
(45) Date of Patent: Aug. 14, 2018

(54) AUTOMATED CEPHALOMETRIC ANALYSIS USING MACHINE LEARNING

(71) Applicant: CephX Technologies Ltd., Herzeliya (IL)

(72) Inventors: Zeev Abraham, Herzeliya (IL); Daniel Abraham, Raanana (IL)

(73) Assignee: CephX Technologies Ltd., Herzeliya (IL)

( * ) Notice: Subject to any disclaimer, the term of this patent is extended or adjusted under 35 U.S.C. 154(b) by 128 days.

(21) Appl. No.: 15/250,284

(22) Filed: Aug. 29, 2016

(65) Prior Publication Data

US 2018/0061054 A1    Mar. 1, 2018

(51) Int. Cl.
| | |
|---|---|
| *G06T 7/00* | (2017.01) |
| *G06T 7/60* | (2017.01) |
| *G06K 9/36* | (2006.01) |
| *A61B 6/14* | (2006.01) |
| *A61B 6/00* | (2006.01) |

(52) U.S. Cl.
CPC .............. *G06T 7/0044* (2013.01); *A61B 6/14* (2013.01); *A61B 6/5217* (2013.01); *G06K 9/36* (2013.01); *G06T 7/60* (2013.01); *G06T 2207/10116* (2013.01); *G06T 2207/20081* (2013.01); *G06T 2207/20084* (2013.01); *G06T 2207/30008* (2013.01); *G06T 2207/30036* (2013.01)

(58) Field of Classification Search
CPC ....... G06T 7/0012; G06T 7/0014; G06T 7/60; G06T 7/74; G06T 2207/20081; G06T 2207/20084; A61B 6/14; A61B 6/501; A61B 6/5217; G06F 19/321; G06F 19/34; G16H 15/00; G16H 30/00; G16H 30/40; G16H 50/20

See application file for complete search history.

(56) References Cited

U.S. PATENT DOCUMENTS

| | | | |
|---|---|---|---|
| 2009/0003667 A1* | 1/2009 | Cheng et al. | 382/128 |
| 2015/0186748 A1 | 7/2015 | Cootes et al. | G06K 9/621 |
| 2016/0038092 A1* | 2/2016 | Golay | A61B 5/7267 433/24 |
| 2016/0203604 A1* | 7/2016 | Gupta et al. | G06T 7/0014 382/128 |

OTHER PUBLICATIONS

Leonardi et al., "An Evaluation of Cellular Neural Networks for the Automatic Identification of Cephalometric Landmarks on Digital Images", Journal of Biomedicine and Biotechnology, vol. 2009, Article ID 717102, 2009, 12 pages.*

(Continued)

*Primary Examiner* — Andrew W Johns
(74) *Attorney, Agent, or Firm* — Intrinsic Law Corp.

(57) ABSTRACT

A system and method are described for automating the analysis of cephalometric x-rays. Included in the analysis is a method for automatic anatomical landmark localization based on convolutional neural networks. In an aspect, the system and method employ a deep database of images and/or prior image analysis results so as to improve the outcome from the present automated landmark detection scheme.

7 Claims, 11 Drawing Sheets

(56) References Cited

OTHER PUBLICATIONS

El-Feghi et al., "Automatic localization of craniofacial landmarks using multi-layer perceptron as a function approximator", Pattern Recognition Letters, vol. 27, 2006, pp. 544-550.*
Pei et al., "Anatomical Structure Sketcher for Cephalograms by Bimodal Deep Learning", Proc. British Machine Vision Conference 2013, 12 pages.*
L. Wolf et al., "Automatic Cephalometric Evaluation of Patients Suffering from Sleep-Disordered Breathing", Tel Aviv University, www.cs.tau.ac.il/~wolf/papers/ceph.pdf.
C. Lindner et al., "Fully automatic cephalometric evaluation using Random Forest regression-voting", p. 1-8, University of Manchester, http://personalpages.manchester.ac.uk/staff/claudia.lindner/_publications/lindner_isbi2015.pdf.
C. Lindner et al., "Robust and Accurate Shape Model Matching using Random Forest Regression-Voting", IEEE Transactions on Pattern Analysis and Machine Intelligence, Sep. 2015, p. 1862-74, 37(9), IEEE.
C. Lindner et al., "Fully Automatic Segmentation of the Proximal Femur Using Random Forest Regression Voting", IEEE Transactions on Medical Imaging, 2013, p. 1-11, IEEE, http://personalpages.manchester.ac.uk/staff/claudia.lindner/_publications/lindner_tmi2013.pdf.
Wikipedia, "Deep Learning—Wikipedia", https://en.wikipedia.org/wiki/Deep_learning, dated Sep. 20, 2016.

* cited by examiner

AUTOMATED CEPHALOMETRIC ANALYSIS USING MACHINE LEARNING

TECHNICAL FIELD

The present disclosure is directed to a system and method for automation of the process of generating cephalometric analyses, including a process for computerized detection and localization of cephalometric landmarks on a cephalometric x-ray image using machine learning as part of said process.

BACKGROUND

Cephalometric analysis is commonly used by dentists and orthodontist to study skeletal relationships in the craniofacial complex. Cephalometric analyses can be used to evaluate a patient's dentofacial proportions, and help doctors recognize abnormalities, predict future changes, and study the success of ongoing treatment plans.

A Cephalometric radiograph is an x-ray radiograph of the head taken in a Cephalometer (Cephalostat) that is a head-holding device introduced in 1931 by Birdsall Holly Broadbent Sr. in USA and by H. Hofrath in Germany. The Cephalometer is used to obtain standardized and comparable craniofacial images on radiographic films. A conventional cephalometric analysis involves the acquisition and initial cephalometric radiograph examination, as well as post-examination reading of the radiograph or related information.

FIG. 1 shows a sequence of frames 100 representative of common steps in current cephalometric procedures according to the prior art, which steps will be discussed in more detail below. Frame A shows a representative cephalometric radiograph as acquired by a modern cephalometer machine. Frame B shows major features of interest in the cephalographic process, including some groups of data found to hold clinical significance by those skilled in the art. Frame C shows individual points of interest related to said major features of interest, overlaid on the cephalographic radiograph of Frame A. Frame D shows a graphical representation of various geometric relationships derived from the positions of the points of interest of Frame C, which can be used to characterize clinical conditions of a patient and which can be used to guide future treatments of the patient.

FIG. 1A shows the cephalometric radiograph 102 of Frame A of FIG. 1, which may be generated from a plurality of base x-ray images to result in the final representation 102. For example, a plurality of individual base x-ray images may be gathered by movement of an x-ray imaging apparatus with respect to the patient (or vice versa) so as to acquire multiple of views of the patient's anatomy, e.g., sweeping the x-ray imager through a lateral 180-degree arc about the stationary patient's head. The plurality of views may then be processed using computer software to yield the shown representative two-dimensional (2D) representation 101, which is stored in a computer memory device as a gray scale cephalometric image, or in some other suitable format. These images may then be examined by human experts, technicians, transmitted for remote analysis, or for computerized post-processing.

Some cephalometric features have been recognized as clinically relevant in the art, shown in FIG. 1B. Examples of such cephalometric landmarks are the sella (marked 'S') and the nasion (marked 'N'). A prime symbol (') usually indicates the point on the skin's surface that corresponds to a given bony landmark (for example, nasion (N) versus skin nasion (N')). FIG. 1B shows the location of some typically required features or groups of landmarks in cephalometric analyses.

FIG. 1C shows individual landmarks (points) of interest as identified on a given patient's cephalometric radiograph, e.g., FIG. 1A. Traditionally, in order to perform the post-examination reading for a patient, dozens of anatomical landmarks representing certain hard or soft tissue anatomical structures are found on the radiograph by a trained human expert. In some examples about ninety points of interest or landmarks are identified and used in the analysis. For example, a technician views the radiograph on a computer screen, and with the aid of a computer mouse, track ball, sensor pad or similar device, annotates various points of interest (landmarks) on the image, e.g., by visually manipulating a cursor position on the screen and selecting the points of interest using a computer mouse button, key, or similar input device. Computer software then marks and stores the indicated points of interest with respect to image 101, which can be saved in a file for further processing, viewing or analysis.

Cephalometric landmarks are used as reference points for the construction of various cephalometric lines or planes and for subsequent numerical determination of cephalometric analysis measurements. FIG. 1D shows an exemplary result 108 of geometrical relationships among the identified landmark points of interest for a patient following acquisition and landmark identification on the patient. The relationships and geometric angles, distances and so on can be quantified to make clinical diagnoses or treatment plans for the patient.

For example, as shown, landmark points can be joined by lines to form axes, vectors, angles, and planes. For example, the sella and the nasion together form the sella-nasion line (SN or S-N).

The resulting cephalometric tracings outline the particular measurements, landmarks, and angles that medical professionals need for treatment. By using a comparative set of angles and distances, measurements can be related to one another and to normative values to determine variations in a patient's facial structure.

One example of a result typically generated in cephalometric analysis is a Jarabak analysis, developed by Joseph Jarabak in 1972. The analysis interprets how craniofacial growth may affect the pre and post treatment dentition. The analysis is based on 5 points: Nasion (N), Sella (S), Menton (Me), Go (Gonion) and Articulare (Ar). They together make a Polygon on a face when connected with lines. These points are used to study the anterior/posterior facial height relationships and predict the growth pattern in the lower half of the face. FIG. 1D shows an example of a Jarabak tracing-part of a Jarabak analysis used by medical professionals.

While the initial x-ray can be completed within minutes, the post X-ray analysis can take much longer. Once the landmarks have been determined by an expert, the various cephalometric analyses are commonly generated electronically used as a way to save time and reduce errors.

However, full automation of the initial manual step of determining the location of landmarks on the x-ray image is challenging due to overlaying structures and inhomogeneous intensity values in radiographic images, as well as anatomical differences across subjects.

Recently, a method has been proposed for automatically annotating objects in radiographic images by using predictive modeling approaches based on decision trees [T. Cootes, C. Lindner, M. Ionita; USPTO publication US2015/0186748 A1]. With this method cephalometric landmarks have been detected [C. Lindner and T. F. Cootes, ISBI 2015]

using Random Forests regression-voting in the Constrained Local Model framework (RFRV-CLM).

A random forest is an ensemble of decision trees that outputs a prediction value. A decision tree is a flowchart-like structure in which each internal node represents a "test" on an attribute, and each branch represents the outcome of the test. A decision tree maps observations about an item to conclusions about the item's target value, in this case the spatial location of one particular landmark. Each decision tree is constructed by using a random subset of the training data, creating a 'forest' of trees. The final prediction of location of a particular landmark is created by combining the decisions of all trees in some way, for example by averaging.

Random forest-type techniques may not provide the accuracy needed in certain applications. For example, the random forest method requires a programmer to define the features being sought ahead of time, and does not permit for automated self-learning in a machine. Therefore, for applications where many (e.g., dozens or hundreds) of features are under investigation, this can be impossible to program and define by a programmer in an acceptable manner, especially given the likely variations in a patient's anatomy and image quality. In addition, random forest methods are best suited for one dimensional array inputs, and as such are at a disadvantage in handling two dimensional cephalometric and similar imagery. Existing random forest based applications therefore can suffer in accuracy and reliability compared to other methods, or even compared to human analysis.

The currently-used step of identifying the required landmarks by hand by a human operator is time-consuming, and the results are inconsistent and subjective. For example, the level of training, skill and experience of operators tasked with locating the landmarks of interest, in FIG. 1C above, can vary. An operator may also provide variable results based on his or her degree of interest in the work, fatigue, eye sight, hand coordination, and other factors. The results could also vary if an operator is very busy, rushed, or under economic or other pressure to finish the task at hand. Even a same operator, working on the same image, and operating with his or her best level of care, would likely generate somewhat different results from attempt to attempt, as the operator's ability to identify an exact pixel on the image under review will not be fully reproducible from time to time. Failures, errors and inaccuracies, or inconsistencies in landmark feature identification will translate directly to errors and inaccuracies in the results of the analysis of the landmarks, and may contribute to liability by the practitioner.

In addition, human operators are relatively inefficient and slow to take in, understand, and annotate the dozens of landmarks of interest on cephalometric radiograph images. Wages paid to well-trained quality technicians who analyze cephalometric images are an economic factor that increases health care costs and reduces profits to practitioners. A tradeoff between haste and accuracy, still limited by the speed at which the human operator works, limit the economic gains obtainable in current cephalometric image analysis systems and methods.

Therefore, there remains a need for an improved landmark identification process that can effectively replace or augment the manual process of choosing a multitude of standardized anatomical points on a cephalometric x-ray. This disclosure addresses a method for doing so, and a system and method for providing cephalometric analyses based on automatic landmarking in a cost-effective, accurate and consistent fashion.

SUMMARY

To address the need for providing accurate and fast cephalometric analyses to dental practitioners, the present disclosure is directed to a method for detecting anatomical landmarks on a cephalometric x-ray image and to incorporating this method in a real-time system and process for generating cephalometric analyses.

In an aspect of the current disclosure, the landmark detection algorithm employs convolutional neural networks (CNN).

A particular embodiment is directed to a method for automated processing a cephalometric image, in a processor-based machine using machine learning steps, so as to provide results for treatment planning and follow-up, comprising receiving a cephalometric image from a user; pre-processing said received cephalometric image, in a processor-based machine, to determine whether the quality of the cephalometric image meets a pre-determined image quality criterion; if said pre-determined image quality criterion is met, carrying out a sequence of automated localization of anatomical landmark points of interest on said cephalometric image, in said processor-based machine, based on machine learning from previously-analyzed cephalometric images; generation of a cephalometric report including analyses results based on said landmarks; formatting said cephalometric report into a user-readable format; and providing said cephalometric report in said user-readable format to said user.

Another particular embodiment is directed to a system for automated analysis of a cephalometric image, provided over a cloud network, comprising a client machine having a user interface, coupled to a cephalometric imaging unit, and further coupled to a communication network; a server, having a processor and implementing a computational neural network (CNN) engine, said CNN engine having a CNN training module and a landmark detection module, said server further being coupled to said communication network and to a database of prior-analyzed cephalometric imagery; said client configured and arranged to deliver a given cephalometric image to said server, over said communication network; and said server configured and arranged to perform a CNN learning and automated anatomical landmark detection process on said given cephalometric image, so as to identify anatomical landmark points of interest in said given cephalometric image, and to output a formatted cephalometric analysis report in a user-readable form.

BRIEF DESCRIPTION OF THE DRAWINGS

For a fuller understanding of the nature and advantages of the present concepts, reference is made to the following detailed description of preferred embodiments and in connection with the accompanying drawings, in which.

DETAILED DESCRIPTION

Aspects of this disclosure are directed to a system and method of providing a cephalometric analysis service to medical professionals. Landmarks are detected with the help of Deep Learning techniques. Deep Learning is a branch of machine learning based on learning representations of data. It utilizes a set of algorithms that attempt to model high-level abstractions in data by using multiple processing layers, with complex structures, composed of multiple non-linear transformations.

Figure 2:
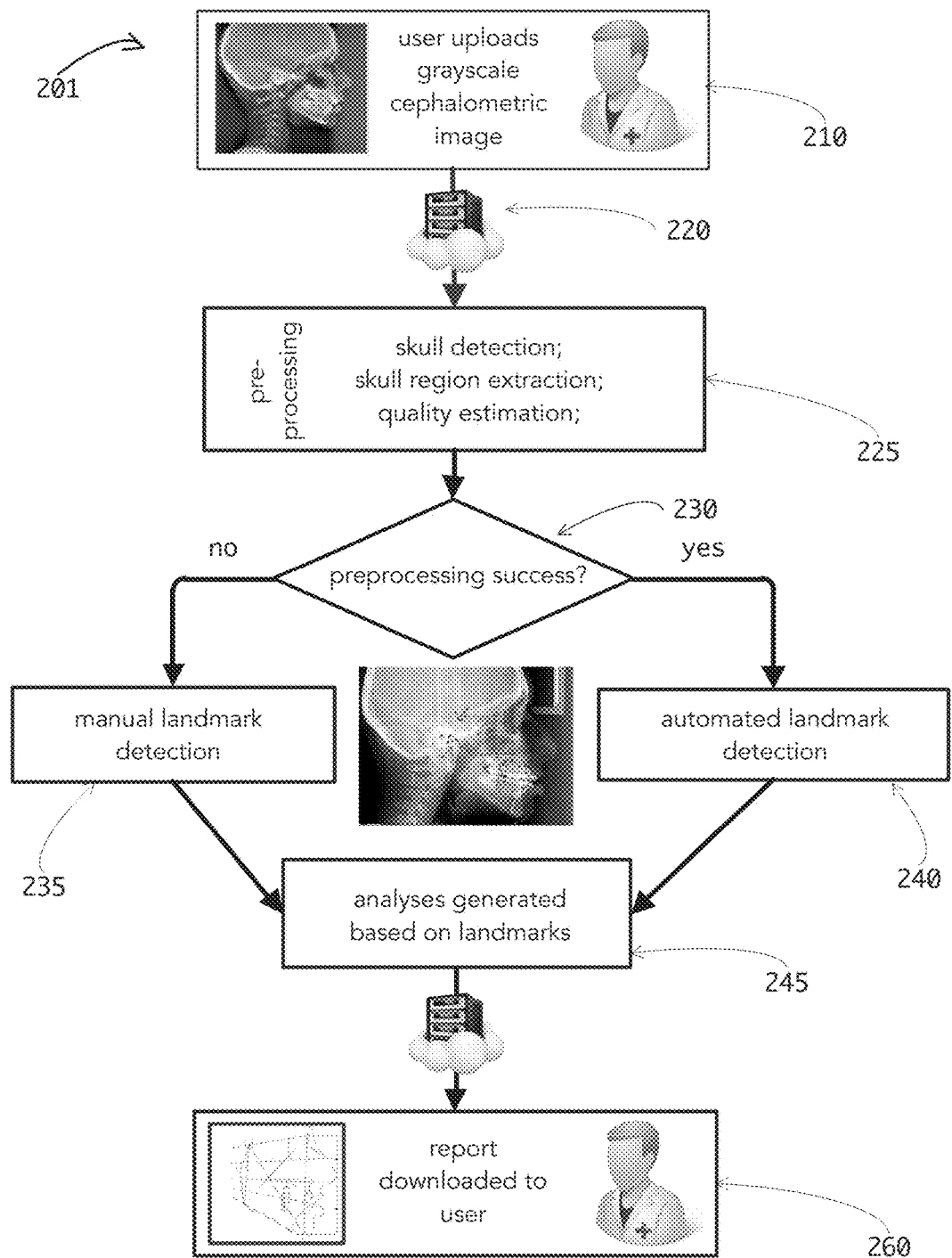
FIG. 2 illustrates an exemplary process for automated cephalometric analysis system using computational neural network and machine learning concepts.

FIG. 2 illustrates an exemplary method 201 for providing professional real-time complete cephalometric analyses to clients.

At step 210 a user uploads a cephalometric x-ray image from a client site to the cloud using a browser, ftp client or similar tool. The client site may include an x-ray imaging apparatus, a client computer system, or other hardware and/or software for generating the cephalometric image or images required. The image or images are provided as electronic files in a preferred embodiment, and may be compressed or encrypted or otherwise formatted for suitable delivery from said client site, over a cloud interface 220, to the server described below.

Once received over a cloud interface 220, the cephalometric image undergoes one or more pre-processing steps 225. For example, the image is evaluated in said pre-processing steps to check if the quality is sufficient for automated analysis. Other pre-processing steps may include skull detection, skull region extraction and others.

Detection of the patient's skull, the skull's position and rotation can be determined using an automated process. In an embodiment, if the skull is not found in an image, further processing may be skipped. If a skull is found, the skull region is extracted and normalized. A normalized skull representation is preferably upright and looking to the right of the flattened/two-dimensional image. It should be appreciated that other examples are equally possible and are comprehended by this disclosure, in which the present examples are provided for illustration and not by way of limitation.

In an embodiment, the cephalometric image undergoes a quality estimation process. At step 230 The image quality is estimated and pre-processing success is determined. If the detected image quality does not meet a specified quality level or threshold, further automated processing may be skipped, and the image may be referred to a human operator for manual landmark detection at step 235, or may be rejected altogether as not containing sufficient detail to enable the present processing and analysis methods. The user may be notified if an uploaded image is of poor quality, fails to meet pre-processing success metrics, or has other issues requiring special attention or causing rejection of the image by the system.

If the pre-processing and quality estimation steps 225, 230 are successful the image proceeds to automated landmark detection at step 240. In a preferred embodiment, a landmark detection algorithm is applied to the image. A method for automated landmark detection can be executed in a server having a processing circuit executing programmed instructions to act on said instructions and image data, as well as stored data as will be described below, to generate useful outputs and analytical results.

In a preferred embodiment, the server performing the automated landmark detection is configured, programmed and adapted to act on certain convolutional neural networks (CNN). CNN is a type of feed-forward artificial neural network in which the connectivity pattern and is inspired by the organization of the animal visual cortex, whose individual neurons are arranged in such a way that they respond to overlapping regions tiling the visual field. Convolutional networks are variations of multilayer perceptrons designed to use minimal amounts of preprocessing. These networks use a special architecture which is particularly well-adapted to classify images.

Figure 3:
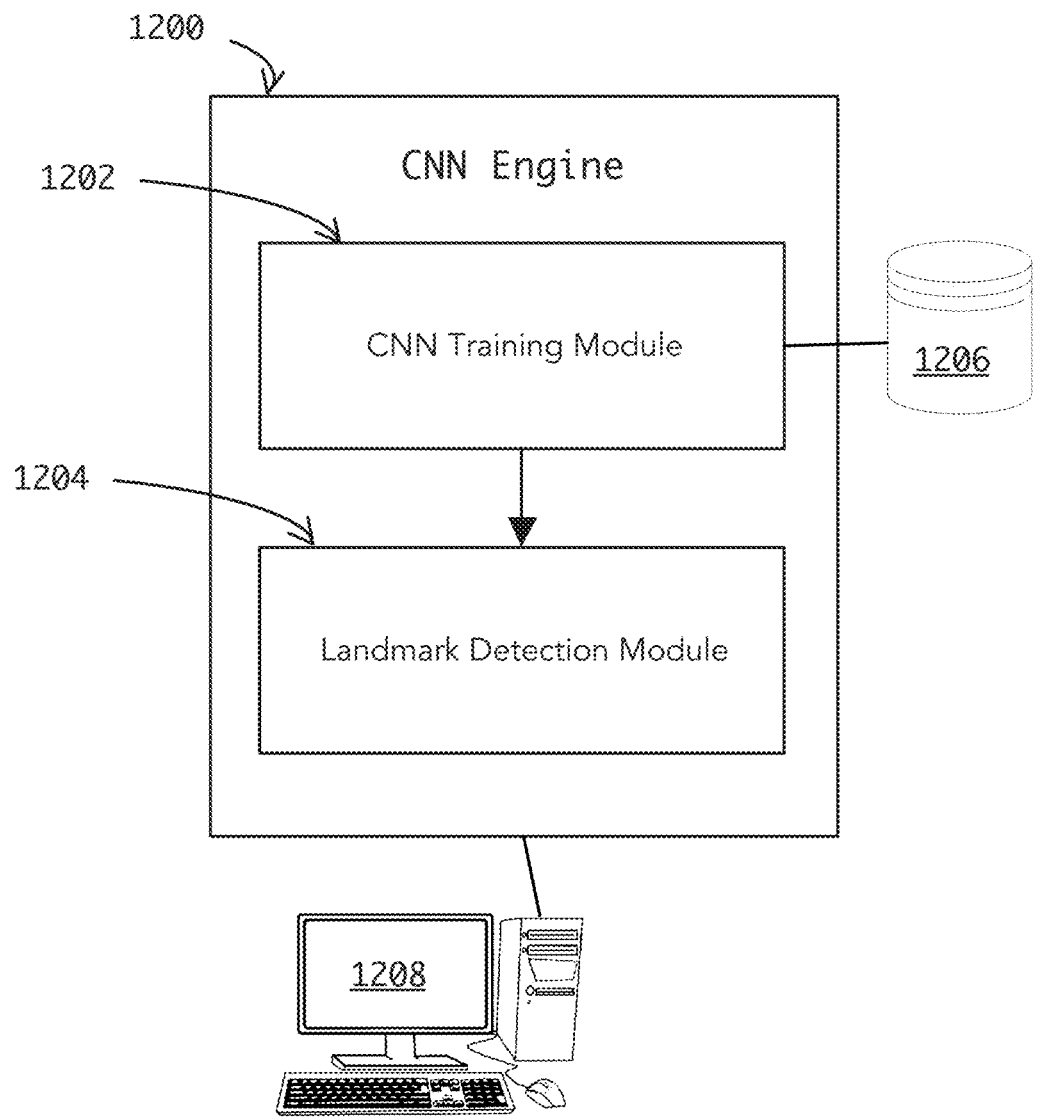
FIG. 3 illustrates an exemplary architecture of a system according to the present disclosure and for carrying out the present method in a CNN Engine.

FIG. 3 illustrates a simplified machine learning system (e.g., a CNN Engine 1200) according to the present disclosure, which includes a plurality of modules to carry out the CNN method described herein and in this context. For example, a CNN Training Module 1202 can be employed to train the CNN system using pre-existing rules and prior store image data. A Landmark Detection Module 1204 may then be used, according to said CNN training, to automatically detect key landmarks in an image. Details of a preferred system and method, using such a CNN Engine, are provided herein.

The CNN Training Module 1202 may comprise electronic circuitry, e.g., application specific integrated circuits (ASIC), general processor unit (GPU), image processing hardware, and/or other computing hardware, firmware, or circuitry. The CNN Training Module 1202 can be implemented in a processor of a computer system, server or similar computing apparatus 1208. The CNN Training Module 1202 is preferably coupled to a memory device holding a plurality of program instructions that are processed, executed, or interpreted by said CNN Training Module 1202.

Figure 1:
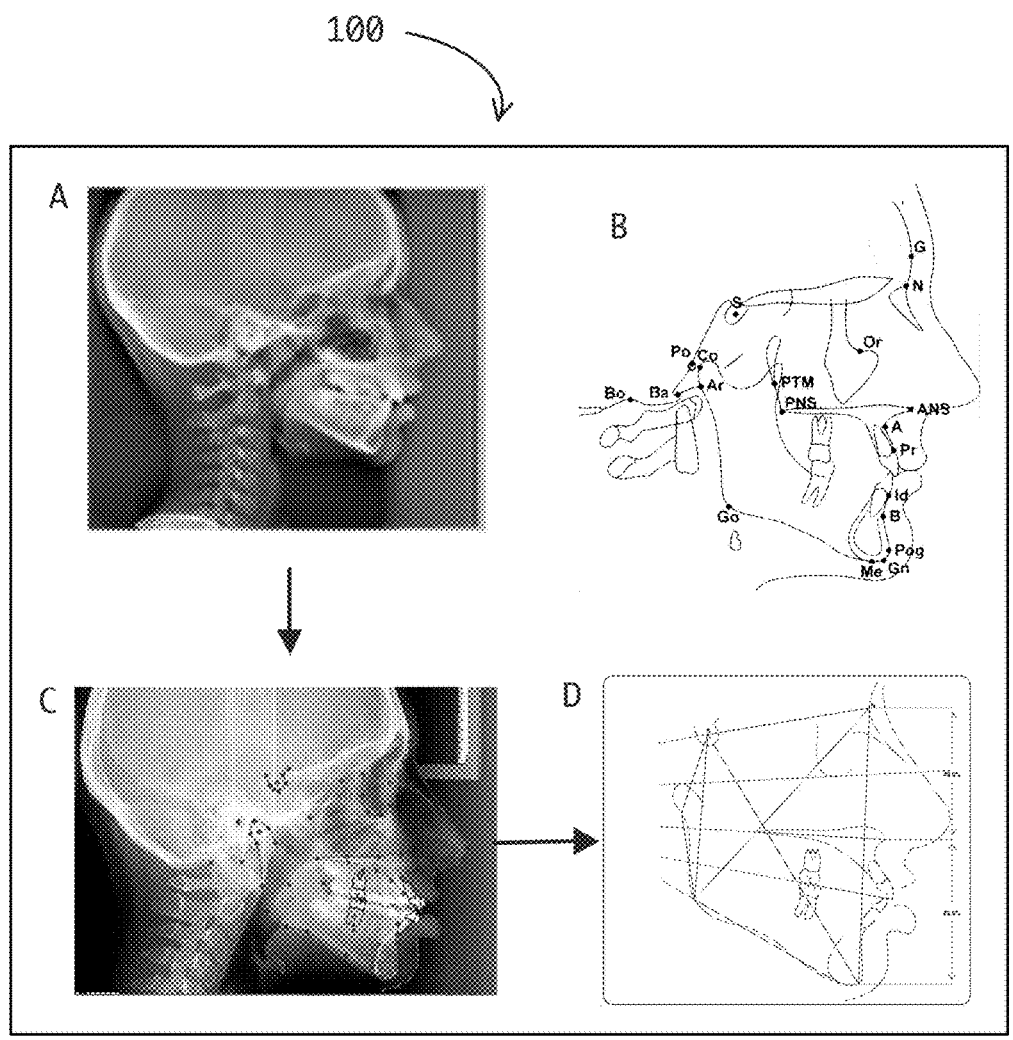
FIG. 1 illustrates some primary stages of traditional cephalometric image analysis according to the prior art.
Figure 1A:
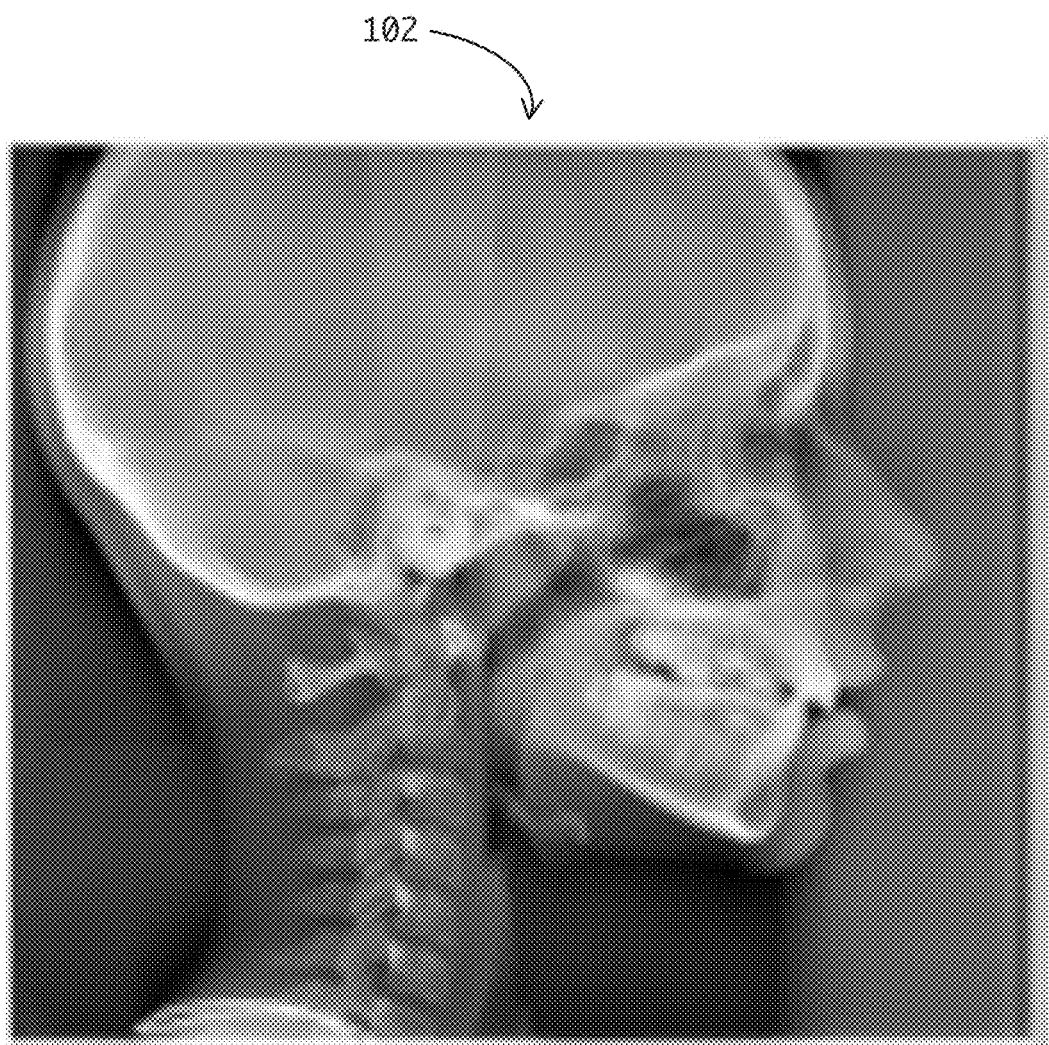
FIG. 1A illustrates an exemplary cephalometric radiograph according to the prior art.
Figure 1B:
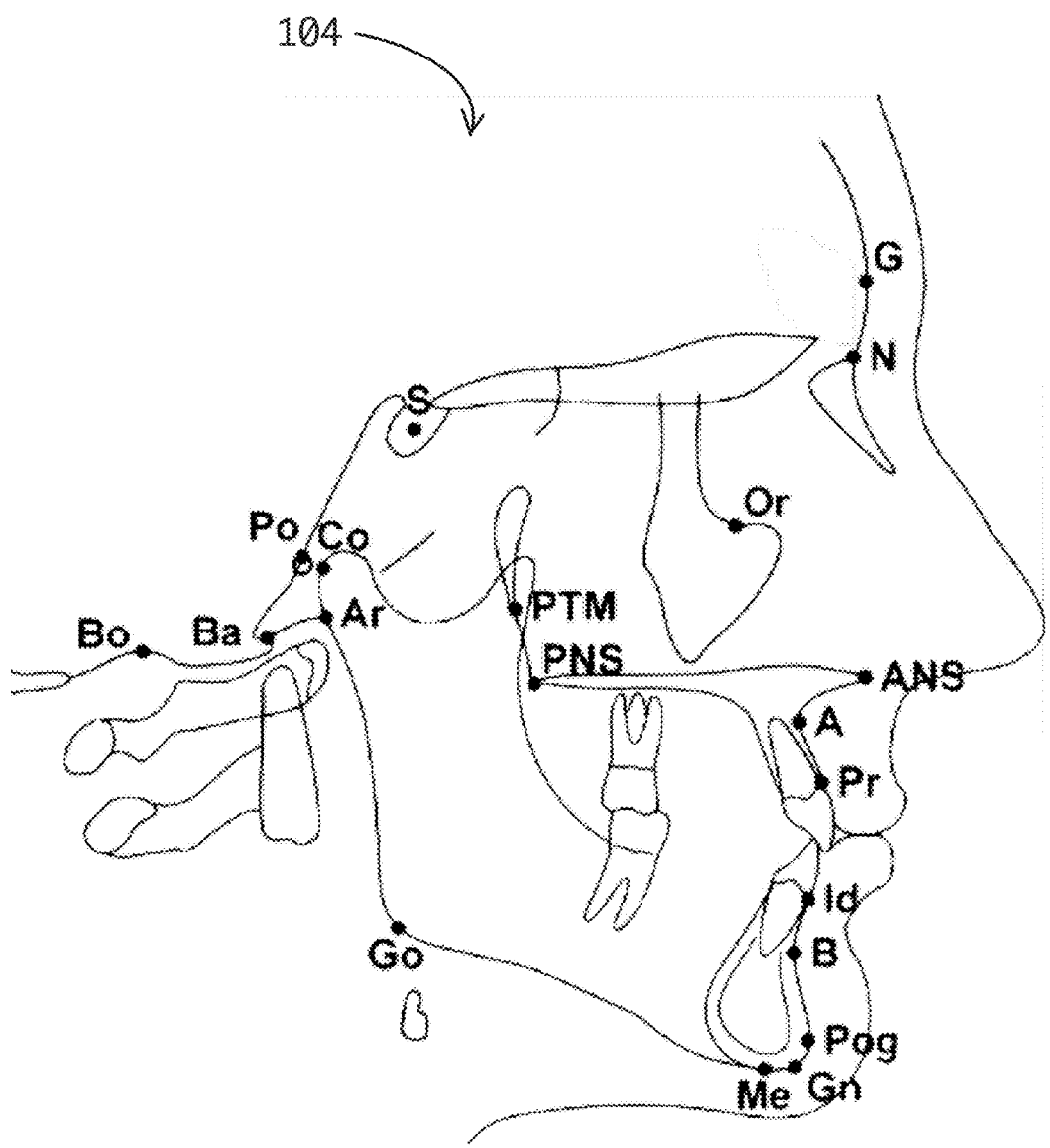
FIG. 1B illustrates a common set of groups or features of clinical interest according to the prior art.
Figure 1C:
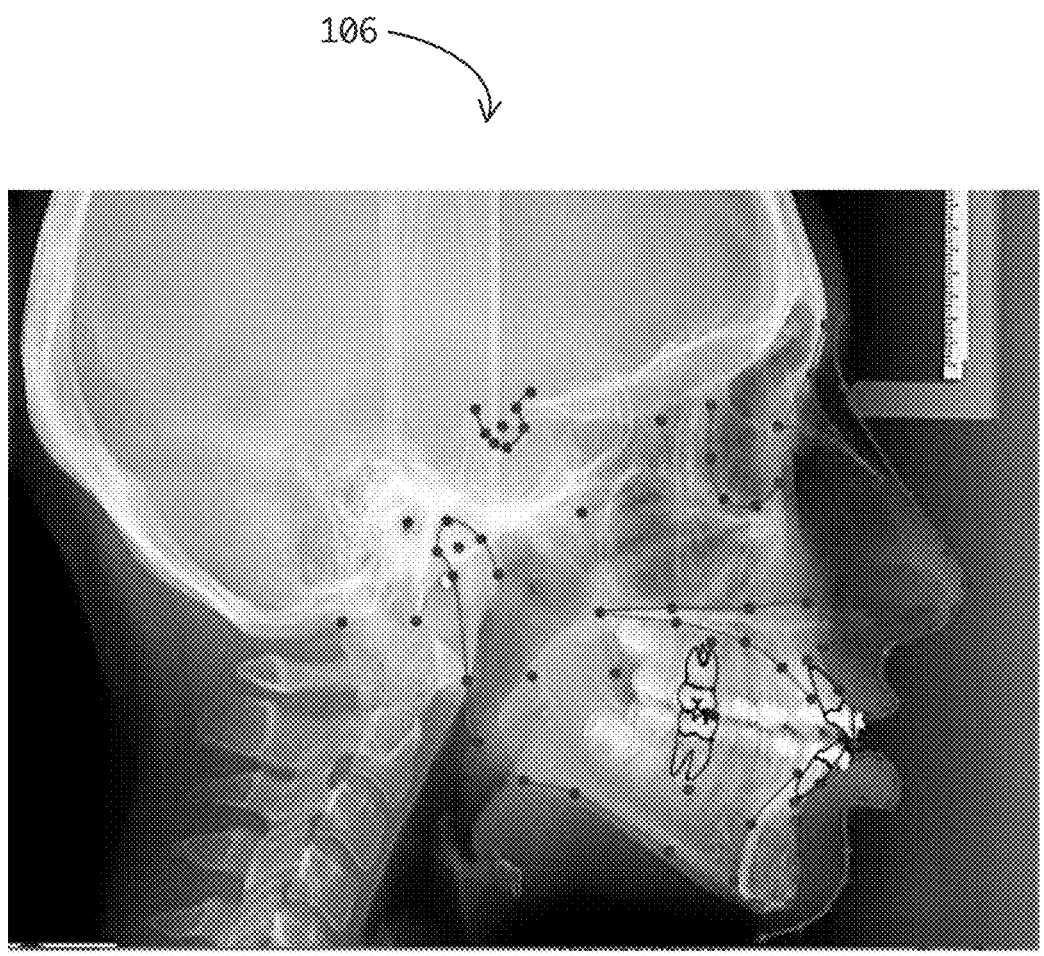
FIG. 1C illustrates an exemplary set of landmark points of interest identified by a human operator corresponding to the groups of features of the previous figure according to the prior art.
Figure 1D:
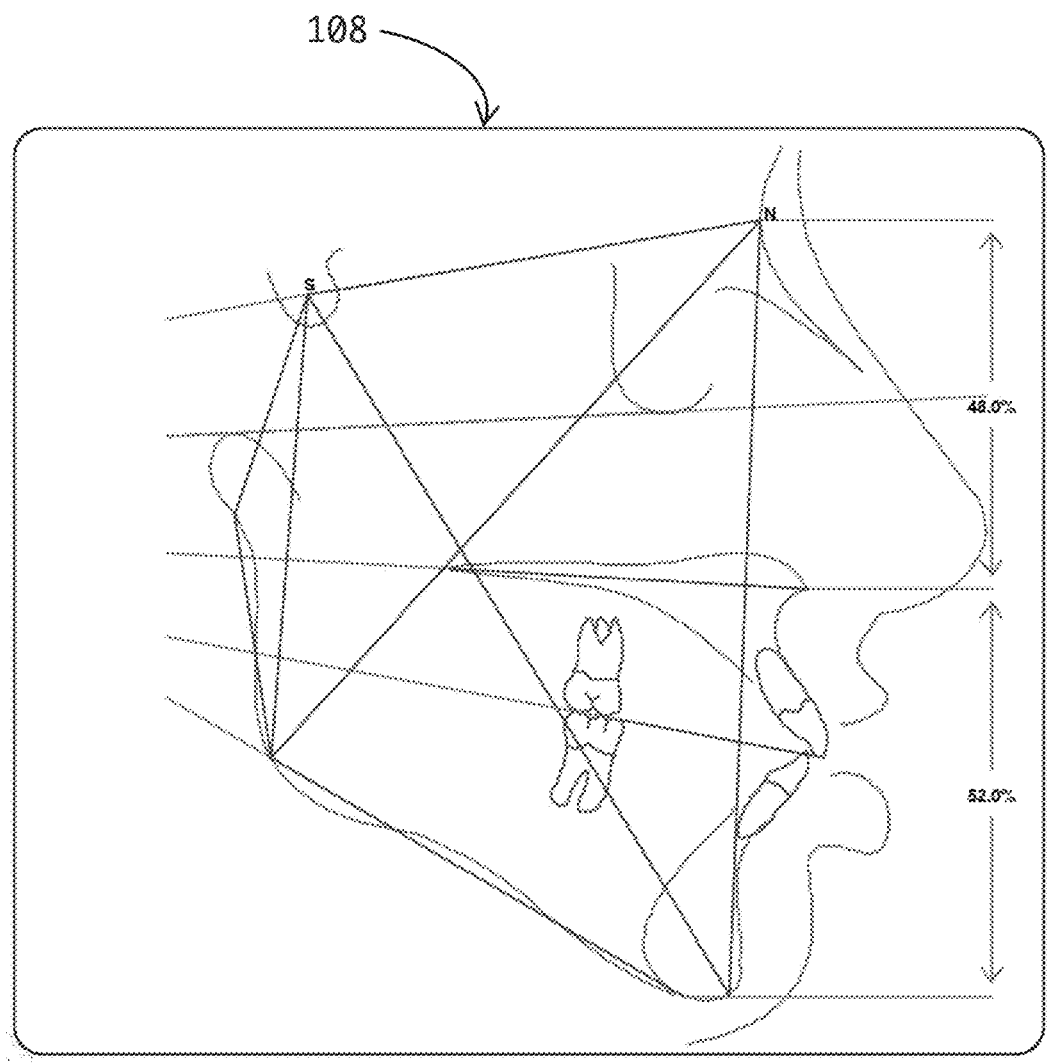
FIG. 1D illustrates an exemplary geometric analysis of the landmark points of interest of the previous figure, which are used to deduce clinical information and to characterize the condition of a patient according to the prior art.

In addition, CNN Training Module 1202 is coupled to a data store 1206 containing a large plurality of pre-stored images relevant to the cephalometric image of interest. For example, the data store 1206 may comprise a digital storage unit holding hundreds, thousands or more prior-taken cephalometric images. The prior-taken images can be all of a same anatomy (e.g., head, face, jaw, teeth, or other portions of patients' bodies), or may comprise different categories of groups of images representing different anatomical structures. In a preferred embodiment, data store 1206 holds many such x-ray cephalometric images of many patients in the head and mouth region, similar to those depicted in FIG. 1A. In addition, data store 1206 may contain analysis results or landmark data associated with the many stored images thereon, similar to those depicted in FIG. 1B, FIG. 1C, or other data indicative of landmarks, structure and analytical results of prior analysis by humans or machines, corresponding to the stored images. These stored images, and optionally the stored landmarks and analytic information associated therewith, are used to train the CNN system using the CNN Training Module discussed.

The following describes an exemplary process for 2D convolutions having 3D kernels with shape num_channels×height×width, where num_channels is a number of channels in the output of the previous layer (the first dimension of the tensor), and width and height are the first two numbers in the convolution specification. In some embodiments, convolutions may be computed at a plurality of spatial locations (e.g., at every pixel) of the input, and sample all input channels. The last number in a specification is a number of filters (sometimes referred to as kernels). For example, convolution 3×3×64 executed with input shape 32×192×192 uses 64 different kernels each of shape 32×3×3.

Activation is a function applied element-wise to an input tensor. ReLU activation is a function that is equal to zero if its argument is less than zero, or to the argument's value otherwise.

Figure 4:
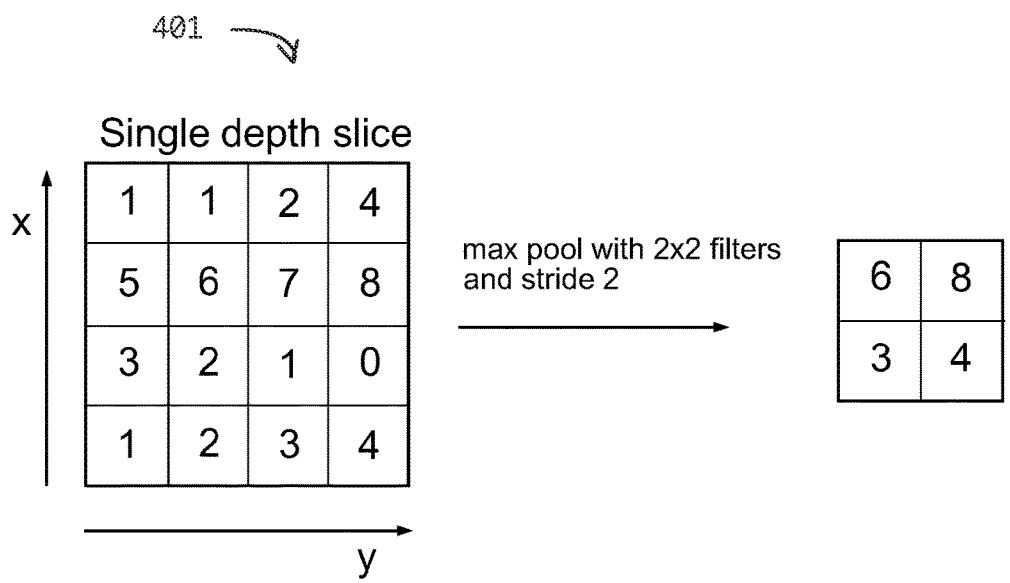
FIG. 4 illustrates a Max pooling method according to the known art.

Pooling layers perform spatial reduction. Specifically, a max pooling operation of size (m×n) replaces an (m×n) area of input channel with the maximum value in the area, as shown in FIG. 4 (see, for example, descriptions of pooling generally, e.g., http URL cs231 n.github.io/convolutional-networks/#pool incorporated herein by reference). The operation is applied channel-wise. The pooling operations in the above architecture have strides equal to pooling size. Preferably, the stride is the shift between pools and thus they do not intersect and there are no gaps between them. The pooling may permit windowing or cropping of the computational field in an image so as to merge, correlate, combine, shrink, reshape or otherwise reconfigure the computational dimensions or areas under consideration in an image.

Dense layers compute matrix multiplication of input vectors by a coefficient matrix. If a layer before a dense layer produces a tensor, then that tensor is reshaped to a vector before multiplication.

Figure 5:
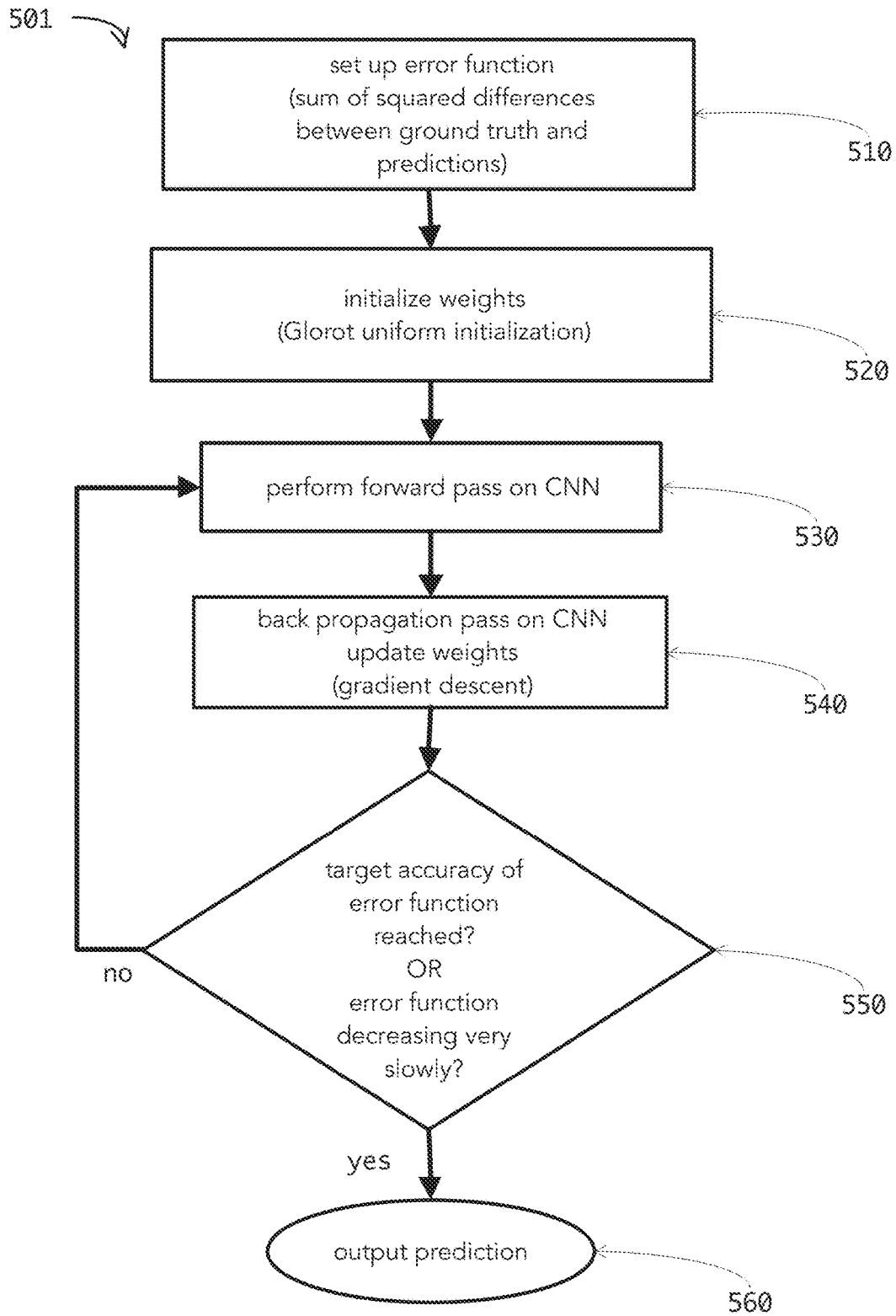
FIG. 5 outlines an exemplary process for training and generating an output prediction.

FIG. 5 illustrates an exemplary series of training steps carried out by the CNN Training Module 1202. The CNN training process 501 uses a dataset of existing cephalometric images, and the landmark points related to them that were located and annotated by human experts (or machines if automated analysis results were available and acceptable). This can be referred to as the "ground truth". The CNN Training Module 1202 then uses data sets stored in data store 1206 to define or approximate an error between the ground truth and predicted values of landmarks of interest at step 510.

In this embodiment, the CNN Training Module 1202 sets up a function to define an error between the ground truth and the algorithm predicted values, i.e., its output. This function may be based on the masked sum of squared errors. Such a mask enables the function to handle missing points in the database, as the tracings in the database vary over the years in the landmarks that were found.

The CNN Training Module 1202 may further determine weights and kernels in the CNN and initialize the same at step 520. The initialization step may use "Glorot uniform" initialization (see for example, http URL jmlr.org/proceedings/papers/v9/glorot10a/glorot10a.pdf, incorporated herein by reference).

The CNN Training Module 1202 may further perform a forward pass to compute the loss value for given input images at step 530. A backward pass then uses the back-propagation technique at step 540 to compute loss gradients by weights (see, e.g., http URL cs231n.github.io/optimization2/, incorporated by reference).

Therefore, the training process of the present system and method includes weights and kernels. The weights may be updated using the AdaDelta optimizer gradient descent method (see, e.g., http URL arxiv.org/abs/1212.5701, incorporated by reference). Those skilled in the art will appreciate that the present steps are typical in a preferred embodiment, and that other steps can be carried out in addition to these steps, or some of these steps can be substituted with equivalent steps to achieve the same or equivalent outcomes.

Step 550 depicts how the training process repeats the forward-back pass and updated model weights until one of the conditions is met: a target error (difference between predicted and ground truth) is reached; or the error is not decreasing or is decreasing very slowly. A threshold can be pre-defined where the training process is considered complete or sufficiently deep and the training process is stopped and an output prediction is generated at step 560. The end result of the training is a set of kernels, biases and weights. These are incorporated in the CNN in the detection phase described below.

As stated, an object of the present system and method is to automatically identify, in a processor-driven machine, landmark points of interest, preferably with some acceptable accuracy and consistency. The input to the process can be considered as one channel (grayscale) image of size 384×384 pixels (tensor of shape 1×384×384). The present 2D Convolution and Dense layers use kernels, weights and biases from the training phase.

Figure 7:
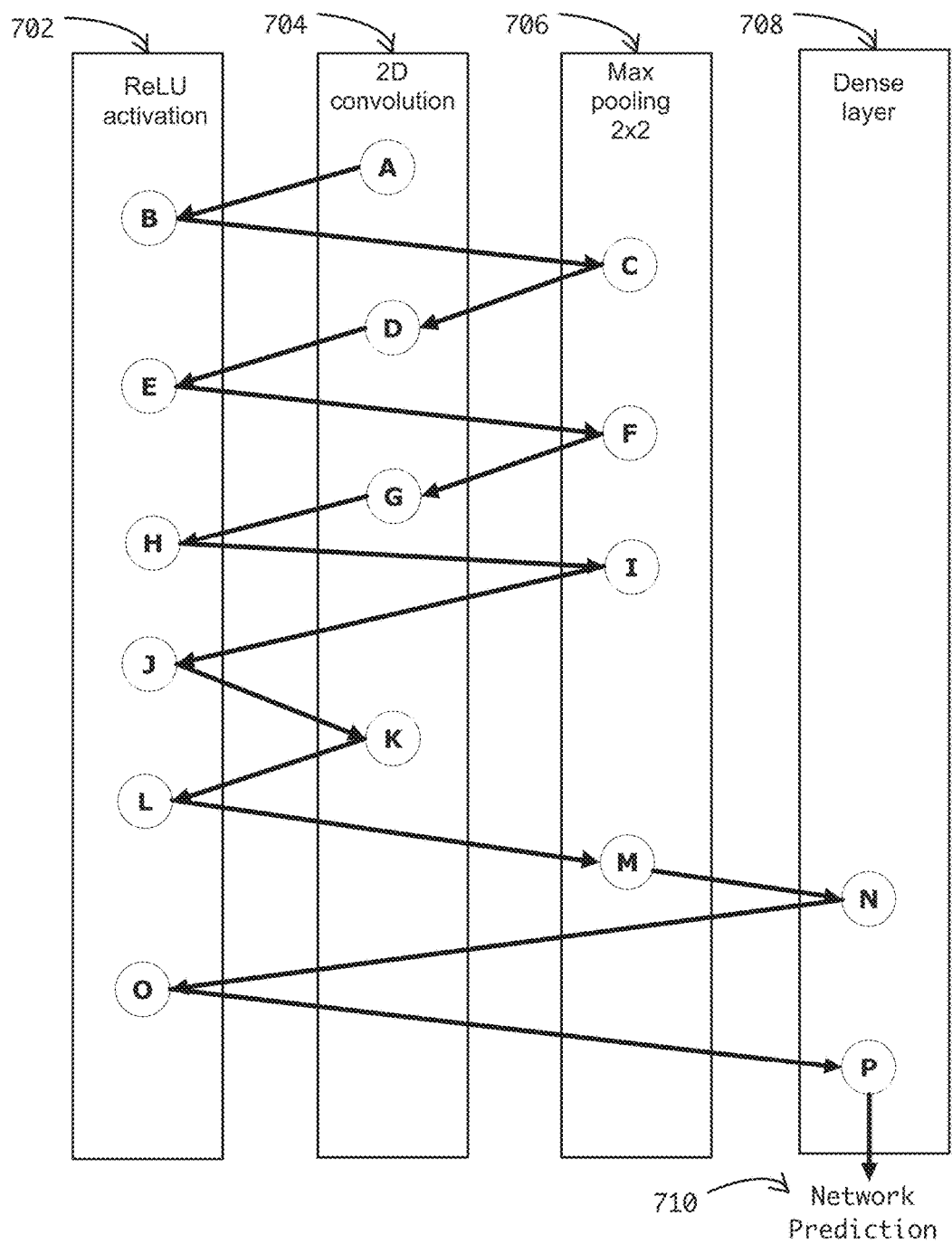
FIG. 7 illustrates an exemplary sequence of steps according to a model for generating a network prediction output.

FIG. 7 illustrates an exemplary landmark points detection process, including sub-processes or steps of ReLU activation 702, 2D convolution 704, Max pooling (2×2) 706 and Dense layer processing 708.

The ReLU step refers to an activation method, which is one type of activation method that can be adapted from the art of neural networks. For the present purposes, ReLU can be a suitable choice of activation methods in some embodiments, for example, owing to its good performance in such points detection applications.

The Dense layer processing step refers to computation of a sum x*W+B, where x is a layer input, and W and B are layer coefficients, W being a matrix and B being a vector. Classical neural networks comprise several dense layers where each dense layer represents one or more "neurons" in the CNN context, or number of columns in matrix W. The convolutional layers thus extract features and the dense layers use said features to perform a regression or classification thereon. In an aspect herein, the dense layers may be used to perform a regression so as to predict point coordinates in an image or data set.

The illustrated steps represent a non-limiting example of the process for points detection, and those skilled in the art may devise or infer similar or equivalent processes with variable steps still consistent with the present disclosure, all of which are comprehended by this disclosure and claims. In the exemplary embodiment depicted, the steps are performed in an order (from top to bottom on the figure as shown) but the ordering of these steps is not necessarily required in all examples.

Here, the process begins at step A with a 2D convolution 5×5×32 (result has shape 32×384×384). At step B a ReLU activation is accomplished (doesn't change shape). Max pooling 2×2 occurs at step C (result has shape 32×192×192). Another 2D convolution is performed at step D on 3×3×64 (result has shape 64×192×192). Another ReLU activation operation on the result is performed at step E (doesn't change shape). This is followed by another Max pooling 2×2 operation at step F (result has shape 32×96×96). A 2D convolution 3×3×64 is carried out at step G (result has shape 64×96×96). ReLU activation on that output is done at step H (doesn't change shape). The next step I performs a Max pooling 2×2 operation (result has shape 64×48×48). The process carries out another ReLU activation at step J (doesn't change shape). 2D convolution 3×3×64 is performed at step K (result has shape 64×48×48). Yet another ReLU activation step is performed at step L (doesn't change shape). And another Max pooling 2×2 is performed at step M (result has shape 64×24×24). Now a Dense layer 36864× 768 process is performed at step N (output is a vector with 768 elements, 36864=64×24×24). This is followed by a ReLU activation at step O (doesn't change shape). And another Dense layer process at 768×186 is performed at step P (output is a vector with 186 elements). The output of this sequence comprises a network prediction 710.

Figure 6:
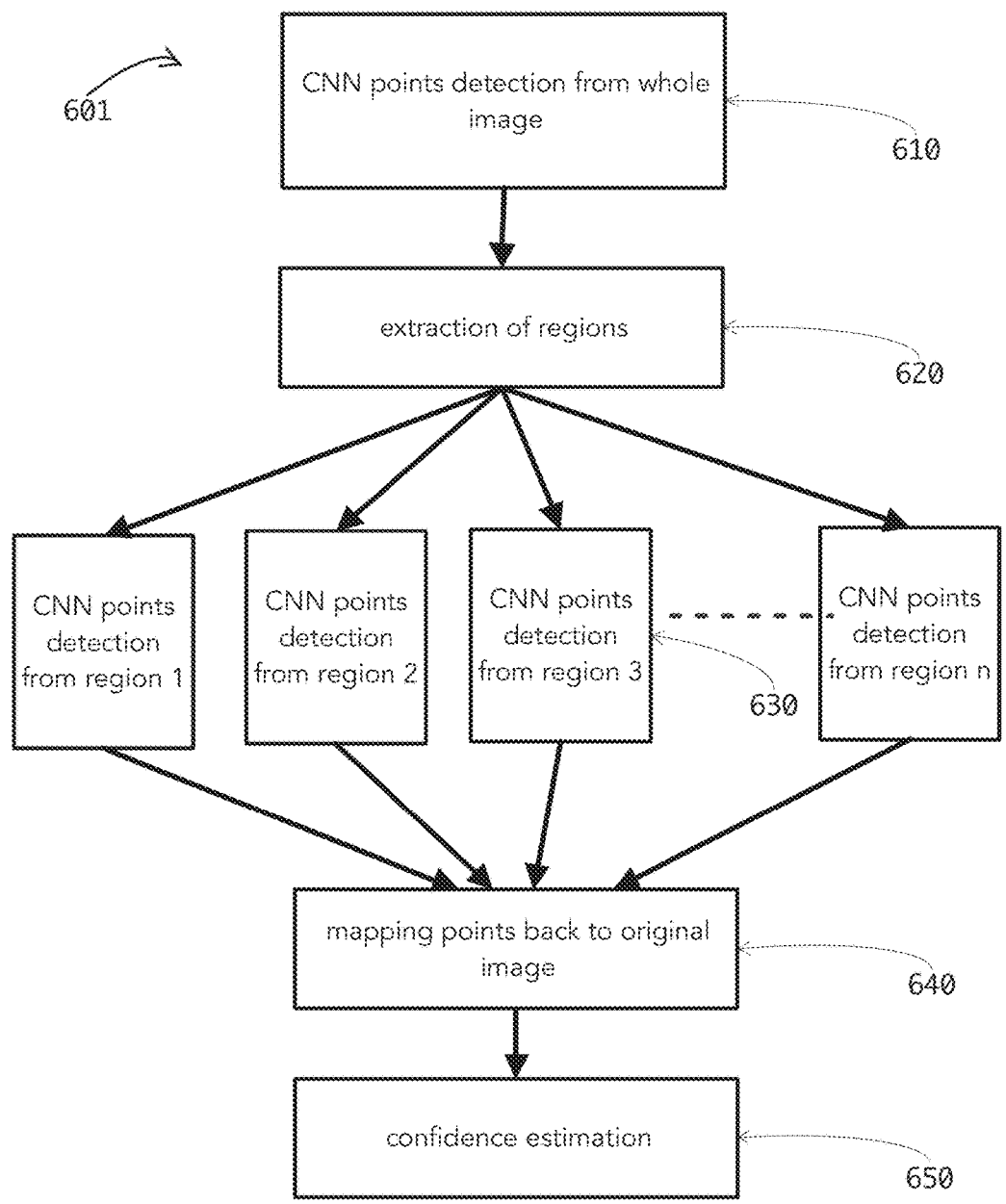
FIG. 6 illustrates an exemplary points detection and regional grouping process to generate confidence estimates.

FIG. 6 illustrates an outline of a detection process 601 as carried out in Landmark Detection Module 1204 in an exemplary embodiment. In the first phase of the detection, at step 610, a CNN detection process is carried out on the whole cephalometric image of interest, for example an x-ray image of a patient's head and jaw. In an attempt to maximize accuracy, the algorithm then attempts to fine-tune the points location as follows.

A complete image may be divided into separate regions, for example defined by groups or sub-groups of landmark points of interest, subsets of anatomy, subsets of pixel regions in an image, and so on. Separate regions are extracted at step 620 corresponding to selected groups of points in the image. In some embodiments approximately 90 points of interest or landmarks are defined. These 90 landmarks can be divided into 12 separate groups of landmark points, each in different area of the skull. The points in each group are refined with a separate CNN-based model for each group in steps 630. Thereafter, all the points are mapped back to the original image at step 640. A confidence estimation is generated corresponding to the results above at step 650. The automated process of extracting and detecting landmark points in the separately identified regions of the image allows for point refinement of the landmark points.

Those reading this disclosure should understand that the exact definition of the groups of landmark points, and the specific number of such groupings are variable. The present examples are given for the sake of illustration and may be adapted differently by those skilled in the art without loss of generality.

Landmark points refinement can be used to split the plurality of landmark points in an entire image into several groups or sub-groups. This helps to achieve better accuracy, for example, because a model that takes into account all points inevitably learns statistical dependency between them. As a result, there is a strong dependency between all the points. While this dependency helps to predict point locations in low quality images (with indistinguishable parts), it also may result in a system shift of some points as the model not only uses visual features to place points, but also information about the usual points position. System shift is a shift when all the points in a group have the same, or almost the same, offset from the correct locations. Also, point refinement models are designed to predict points that are spatially close to each other. Thus the input image for a refinement model does not have to include the whole skull but only a specific part of the skull, so the input image is smaller and at the same time contains more detail. The input image size has a direct influence on the model size. The bigger the input image, the more coefficients the model has and the harder it is to train, both in terms of training time and convergence.

The points refinement process is set up in a way that all refinement models are independent so there can be an arbitrary number of refinement models. In one embodiment, each refinement model is trained according to the training process of FIG. 5, with the exception that only the corresponding subset of points is used and input images are cropped to contain only the relevant part of the skull. In its prediction phase, each refinement model uses its own coefficients (kernels, biases and weights) obtained during its own training phase.

During the refinement stage each refinement model may be used to obtain predictions for a corresponding group of point and to estimate the prediction confidence. If the point confidence is above or equal to a controllable threshold then the corresponding point is updated to use the refined coordinates, otherwise the initial prediction is kept for that point.

In one preferred embodiment, several (e.g., five) point refinement models are used, as described below. These models are not intended to be comprehensive or limiting. Those skilled in the art will appreciate how to extend this discussion to many models and anatomical and clinical analyses, and even to non-clinical situations involving the identification of groups of landmark points in an image based on the present techniques.

As a first example, consider the so-called Sella group model. This model is a commonly observed system shift of Sella points. Statistics learned by the initial model had a strong an influence on the location of Sella points. So in an embodiment, the present system and method can reduce or eliminate this dependency. As an example, the Sella group model may accept a single channel grayscale images of size 128×128 pixels and predicts the Sella group's points of interest corresponding to, e.g., Center Sella, Top-Left Sella, Mid-Left Sella, Bottom-Left Sella, Low-Mid Sella, Mid-Right Sella, Top-Right Sella and the Superior-Right Sella points. Such points may be referred to in an arbitrary, or in a proprietary or in a standardized numbering scheme, for example as points: 1, 2, 3, 4, 5, 6, 7, 8. The present examples are of course not limiting or exhaustive, and other naming and numbering schemes or points of interest in a group can be defined.

For the Sella group model architecture, the following steps (described further herein) may be employed:
 1. 2D convolution 5×5×32 (output shape: 32×128×128)
 2. ReLU activation (doesn't change shape)
 3. Max pooling 2×2 (result has shape 32×64×64)
 4. 2D convolution 3×3×64 (output shape: 64×64×64)
 5. ReLU activation (doesn't change shape)
 6. Max pooling 2×2 (result has shape 64×32×32)
 7. 2D convolution 3×3×64 (output shape: 64×32×32)
 8. ReLU activation (doesn't change shape)
 9. Max pooling 2×2 (result has shape 64×16×16)
 10. 2D convolution 3×3×64 (output shape: 64×16×16)
 11. ReLU activation (doesn't change shape)
 12. Max pooling 2×2 (result has shape 64×8×8)
 13. Dense layer 4096×256 (output is a vector with 256 elements).
 14. ReLU activation (doesn't change shape)
 15. Dense layer 256×16 (output is a vector with 16 elements). The output of this layer is the network prediction for corresponding group.

In another example a Nose group model is employed. This model together with the following "nasal-bone" model were designed to break the dependency between the soft nose contour and the hard nose. It was found that these groups have a strong a dependency between them that resulted in shifts of the hard nose points after the soft nose points, which embodiments of this invention address. It was also observed that for some images soft nose points we following points of lower jaw.

The Nose group model accepts single channel grayscale images of size 128×128 pixels and predicts a set of Nose group points of interest, for example: Soft nose 1, Soft nose 2, Soft nose 3, Soft nose 4, Soft nose 5, . . . , Soft nose N, and the Frontale points. As before, these points in the Nose group could be referred to in a shorthand manner, e.g., as points: 75, 76, 77, 78, 79, 80, 81, or any other reference found convenient.

For the Nose group model architecture, the following steps (described further herein) may be employed:
1. 2D convolution 5×5×32 (output shape: 32×128×128)
2. ReLU activation (doesn't change shape)
3. Max pooling 2×2 (result has shape 32×64×64)
4. 2D convolution 3×3×64 (output shape: 64×64×64)
5. ReLU activation (doesn't change shape)
6. Max pooling 2×2 (result has shape 64×32×32)
7. 2D convolution 3×3×64 (output shape: 64×32×32)
8. ReLU activation (doesn't change shape)
9. Max pooling 2×2 (result has shape 64×16×16)
10. 2D convolution 3×3×64 (output shape: 64×16×16)
11. ReLU activation (doesn't change shape)
12. Max pooling 2×2 (result has shape 64×8×8)
13. Dense layer 4096×384 (output is a vector with 384 elements).
14. ReLU activation (doesn't change shape)
15. Dense layer 384×14 (output is a vector with 14 elements). Output of this layer is the network prediction for the corresponding group.

In a third example, Hard-Nose group model is employed. This model accepts single channel grayscale images of size 128×128 pixels and predicts the following points: Cranial base parallel, Nasion, Anterior Mid-Nasal Bone, Nasal Bone Apex, Posterior Mid-Nasal bone, Posterior nasal bone. The present models may also include other points of interest in the vicinity of a group of points as described, for example a "SOR" point in the vicinity of the Hard nose group of points, which is not part of the Hard nose group itself, but is located relatively close to them.

For the Nasal bone group model architecture, the following steps (described further herein) may be employed:
1. 2D convolution 5×5×32 (output shape: 32×128×128)
2. ReLU activation (doesn't change shape)
3. Max pooling 2×2 (result has shape 32×64×64)
4. 2D convolution 3×3×64 (output shape: 64×64×64)
5. ReLU activation (doesn't change shape)
6. Max pooling 2×2 (result has shape 64×32×32)
7. 2D convolution 3×3×64 (output shape: 64×32×32)
8. ReLU activation (doesn't change shape)
9. Max pooling 2×2 (result has shape 64×16×16)
10. 2D convolution 3×3×64 (output shape: 64×16×16)
11. ReLU activation (doesn't change shape)
12. Max pooling 2×2 (result has shape 64×8×8)
13. Dense layer 4096×384 (output is a vector with 384 elements).
14. ReLU activation (doesn't change shape)
15. Dense layer 384×14 (output is a vector with 14 elements). Output of this layer is the network prediction for the corresponding group.

The next two group of points that were split are points of the upper and lower jaw. When analyzing predictions of the whole head model we found that one of the most difficult cases for the model to process is when the patient's mouth is open or partially open. In most images of the training dataset, the patient's mouth is closed and the initial model memorizes this relation. As a result, when the patient's mouth is opened, the model correctly detects the lower jaw points and shifts all other points towards them.

A Lower jaw group model was also considered in a fourth example. The model accepts single channel grayscale images of size 160×160 pixels and predicts some or all of the following points of interest: Lower central incisal edge, Lower central root apex, Lower molar occlusal edge, Lower molar mesial root apex, Incision at lower central, B point, Supra pogonion, Pogonion, Gnathion, Menton, Geniod, High geniod, Supra-lingual contact, Soft submental, Supra mental, Soft gnathion, Soft pogonion, Soft supra-pognion, and Soft B points.

For the Lower jaw group model architecture, the following steps (described further herein) may be employed:
1. 2D convolution 5×5×32 (output shape: 32×160×160)
2. ReLU activation (doesn't change shape)
3. Max pooling 2×2 (result has shape 32×80×80)
4. 2D convolution 3×3×64 (output shape: 64×80×80)
5. ReLU activation (doesn't change shape)
6. Max pooling 2×2 (result has shape 64×40×40)
7. 2D convolution 3×3×64 (output shape: 64×40×40)
8. ReLU activation (doesn't change shape)
9. Max pooling 2×2 (result has shape 64×20×20)
10. 2D convolution 3×3×64 (output shape: 64×20×20)
11. ReLU activation (doesn't change shape)
12. Max pooling 2×2 (result has shape 64×10×10)
13. Dense layer 6400×384 (output is a vector with 384 elements).
14. ReLU activation (doesn't change shape)
15. Dense layer 384×48 (output is a vector with 48 elements). Output of this layer is the network prediction for the group.

In a fifth example, an Upper jaw group model was employed. The model accepts single channel grayscale images of size 192×192 pixels and predicts, for example, the following points of interest: Upper central incisal edge, Upper central root apex, Upper molar occlusal edge, Upper molar mesial root apex, Prosthion at upper incisor, A-Point, ANS, Palatal elevation, Distal elevation point, Upper mid palate, PNS, Lower posterior palate, Lower mid palate, High palatal curve, Low palatal curve, Upper lip 1, Upper lip 2, Upper lip 3, Upper lip 4, Upper lip 5, Soft A, and the Subnasale points.

For the Upper jaw group model architecture, the following steps (described further herein) may be employed:
1. 2D convolution 5×5×64 (output shape: 64×192×192)
2. ReLU activation (doesn't change shape)
3. Max pooling 3×3 (result has shape 64×43×43)
4. 2D convolution 3×3×64 (output shape: 64×43×43)
5. ReLU activation (doesn't change shape)
6. Max pooling 2×2 (result has shape 64×22×22)
7. 2D convolution 3×3×64 (output shape: 64×22×22)
8. ReLU activation (doesn't change shape)
9. Max pooling 2×2 (result has shape 64×11×11)
10. 2D convolution 3×3×64 (output shape: 64×11×11)
11. ReLU activation (doesn't change shape)
12. Max pooling 2×2 (result has shape 64×6×6)
13. Dense layer 2304×384 (output is a vector with 384 elements).
14. ReLU activation (doesn't change shape)
15. Dense layer 384×44 (output is a vector with 44 elements). The output of this layer is the network prediction.

There may be points not included in the refinement process. For example, the points that are predicted well by the initial model may not need to be included. Or, points that are not spatially close to each other may not support a small enough model. Or yet, points that are located in areas of the image that are usually quite noisy where even human experts may have difficulty locating them, and may not be included.

To estimate the network confidence, the trained network is converted to a fully convolutional network (FCN). See for example, generally, http URL cs231n.github.io/convolution-alnetworks/#convert regarding FCN networks, incorporated herein by reference.

After this step the network is able to take arbitrary sized images and produce several outputs depending on the input image size. These outputs correspond to different spatial locations in the original image taken with some step that depends on network architecture.

For example, a network that has 4 Maxpool layers of size 2×2 and input size 128×128 pixels, after conversion to FCN can take an image of any size, and for any size larger than 128×128 it will perform the same way as if the original network was executed several times on crops of size 128×128 pixels taken with step 16 pixels ($16=2^4$). For this particular example if FCN is provided with input of size 160×160 pixels, it will output 9 predictions corresponding to 9 spatial locations with step 16 pixels.

The same result may be achieved with manually extracted crops and execution of the original (not FCN) network several times (9 times in this particular case) but the former approach is much more effective.

Thus we obtain several predictions for each point and then statistical methods are used to calculate the probability that all predictions are within a specified confidence interval (which in the 2D case is an ellipse with a specified effective radius).

Under the assumption that the points have a 2D Gaussian distribution, we have the following formula for the probability p that all the points are inside an ellipse with effective radius R (and area ρ):

$$p = 1 - e^{\left(-\frac{\rho^2}{2\pi^2|\Sigma|}\right)} = 1 - e^{\left(-\frac{R^4}{2|\Sigma|}\right)},$$

where Σ is an average covariation matrix.

The input image used to estimate confidence should be carefully prepared. In particular, the input image should take into account that prediction effectively executed on crops taken at different spatial locations and that all crops should include region that contains target points.

At the same time it imposes restrictions to the model training process. During the training phase model should face images with a similar scale to those that it will face with FCN.

Another possible issue may arise if initial predictions have large offsets from the correct positions. In this case effective crops may include not full sets of points but only some of them. To solve this potential issue we first execute the model in single prediction mode (when input image has exactly the same size as in the original model) and then use the obtained predictions to extract crops for confidence estimation.

Those skilled in the art will appreciate that the foregoing features and examples are illustrative of useful ways in which the present system and method can be implemented, but that other implementations including other features can be implemented as well. Similarly, those skilled in the art will understand that the above examples and aspects are not all required for operation of the present system and method. Such features and embodiments may be included as needed for a given application.

The present invention should not be considered limited to the particular embodiments described above, but rather should be understood to cover all aspects of the invention as fairly set out herein. Various modifications, equivalent processes, as well as numerous structures to which the present invention may be applicable, will be readily apparent to those skilled in the art to which the present invention is directed upon review of the present disclosure.

What is claimed is:

1. A method for automated processing a cephalometric image, in a processor-based machine using machine learning steps, so as to provide results for treatment planning and follow-up, comprising:
   receiving a cephalometric image from a user;
   pre-processing said received cephalometric image, in a processor-based machine, to determine whether the quality of the cephalometric image meets a pre-determined image quality criterion;
   if said pre-determined image quality criterion is met, carrying out a sequence of automated localization of anatomical landmark points of interest on said cephalometric image, in said processor-based machine, based on machine learning from previously-analyzed cephalometric images;
   generation of a cephalometric report including analyses results based on said landmarks;
   formatting said cephalometric report into a user-readable format; and
   providing said cephalometric report in said user-readable format to said user.

2. The method of claim 1, further comprising generating a two-dimensional cephalometric X-ray image of a subject prior to receiving said image from the user.

3. The method of claim 1, receiving said cephalometric image comprising receiving the cephalometric image over a cloud-based communication network.

4. The method of claim 1, further comprising authenticating said user with said processor-based machine, over a communication network, wherein said processor-based machine comprises a server with a user interface.

5. The method of claim 1, said automated localization step comprising using a convolutional neural network (CNN) process executed in said processor-based machine, and employing information from said previously-analyzed cephalometric images, so as to identify said anatomical landmark points of interest in said cephalometric image.

6. The method of claim 1, further comprising pooling of data in a computational space within said cephalometric image.

7. The method of claim 1, generation of said cephalometric report comprising determining a plurality of diagnostic metrics based on geometric relationships between said anatomical landmark points of interest.

* * * * *